US012564355B2

(12) United States Patent
Seba et al.

(10) Patent No.: US 12,564,355 B2
(45) Date of Patent: Mar. 3, 2026

(54) MICRO MOTION DETECTION FOR DETERMINING AT LEAST ONE VITAL SIGN OF A SUBJECT

(71) Applicant: Linet spol s.r.o., Slany (CZ)

(72) Inventors: Petr Seba, Bartosovice v Orlickych horach (CZ); Vladimír Kolar, Slany (CZ); Ondrej Bradac, Prague (CZ)

(73) Assignee: Linet spol s.r.o., Slany (CZ)

( * ) Notice: Subject to any disclaimer, the term of this patent is extended or adjusted under 35 U.S.C. 154(b) by 817 days.

(21) Appl. No.: 17/291,916

(22) PCT Filed: Nov. 27, 2019

(86) PCT No.: PCT/IL2019/051295
§ 371 (c)(1),
(2) Date: May 6, 2021

(87) PCT Pub. No.: WO2020/115733
PCT Pub. Date: Jun. 11, 2020

(65) Prior Publication Data
US 2022/0007948 A1     Jan. 13, 2022

(30) Foreign Application Priority Data

Dec. 2, 2018    (IL) .......................................... 263409

(51) Int. Cl.
*A61B 5/318*        (2021.01)
*A61B 5/00*         (2006.01)
(Continued)

(52) U.S. Cl.
CPC ........ *A61B 5/6801* (2013.01); *A61B 5/02108* (2013.01); *A61B 5/0245* (2013.01);
(Continued)

(58) Field of Classification Search
CPC .................. A61B 5/318; A61B 5/0205; A61B 5/02108; A61B 5/031; A61B 5/11; A61B 5/6823;
(Continued)

(56) References Cited

U.S. PATENT DOCUMENTS 5,367,292 A * 11/1994 Szoke .................. A61B 5/0878
600/529
7,396,331 B2     7/2008 Mack et al.
(Continued)

FOREIGN PATENT DOCUMENTS

| WO | 2015051770 A1 | 4/2015 |
| WO | 2017220055 A1 | 12/2017 |
| WO | 2017220056 A1 | 12/2017 |

OTHER PUBLICATIONS

WIPO, European Patent Office, International Search Report, in International Application No. PCT/IL2019/051295 filed Nov. 27, 2019, mailed Mar. 16, 2020.
(Continued)

*Primary Examiner* — Pamela M. Bays
(74) *Attorney, Agent, or Firm* — Thedford I. Hitaffer; Hitaffer, PLLC

(57) ABSTRACT

A system and method for determining a vital sign of a subject includes a plurality of pressure sensors configured to be placed in a vicinity of the subject to sense movements of the subject's skin within a region on the skin and generate data corresponding to the region. The data comprises signals indicative of a physiological events differentiated in time and intensity. A control unit comprising an analyser processing utility receives the sensing data, generates a pressure variation profile for the pressure sensors associated with each region, identifies predetermined signatures indicative of at least one physiological event of the subject; generate signature data thereof; extract at least one time stamp from
(Continued)

the signature data; and generate vital sign data indicative of at least one vital sign of the subject based thereon.

14 Claims, 10 Drawing Sheets

(51) Int. Cl.

| | |
|---|---|
| *A61B 5/021* | (2006.01) |
| *A61B 5/0245* | (2006.01) |
| *A61B 5/03* | (2006.01) |
| *A61B 5/0205* | (2006.01) |
| *A61B 5/11* | (2006.01) |

(52) U.S. Cl.
CPC .............. *A61B 5/031* (2013.01); *A61B 5/318* (2021.01); *A61B 5/6814* (2013.01); *A61B 5/6823* (2013.01); *A61B 5/6892* (2013.01); *A61B 5/0205* (2013.01); *A61B 5/11* (2013.01); *A61B 2562/0247* (2013.01)

(58) Field of Classification Search
CPC .......... A61B 5/6892; A61B 2562/0247; A61B 5/0245; A61B 5/6814; A61B 5/6801
See application file for complete search history.

(56) References Cited

U.S. PATENT DOCUMENTS

| | | | |
|---|---|---|---|
| 7,786,267 B2 | 8/2010 | Zurawski et al. | |
| 2002/0045921 A1* | 4/2002 | Wolinsky ............. | A61N 1/3787 |
| | | | 607/61 |
| 2005/0107722 A1* | 5/2005 | Ozaki ................. | A61B 5/6887 |
| | | | 600/587 |
| 2005/0124864 A1 | 6/2005 | Mack et al. | |
| 2008/0275314 A1* | 11/2008 | Mack ....................... | A61B 5/11 |
| | | | 600/595 |
| 2011/0087113 A1 | 4/2011 | Mack et al. | |
| 2011/0166459 A1* | 7/2011 | Kopetsch .............. | A61B 5/021 |
| | | | 600/485 |

OTHER PUBLICATIONS

WIPO, European Patent Office, Written Opinion, in International Application No. PCT/IL2019/051295 filed Nov. 27, 2019, mailed Mar. 16, 2020.

* cited by examiner

100

110

Voltage vs milliseconds

Measurement cycles vs time

Cardiac stroke cycles vs time

Cardiac stroke cycles vs time

Method for determining a vital sign of a subject 900

Step 940 — Receiving sensing data

Step 942 — Analyzing sensing data

Step 944 — Generating pressure variation profile

Step 946 — Identifying predetermined signatures

Step 948 — Extracting time stamps

Step 950 — Generating data indicative of at least one vital sign

MICRO MOTION DETECTION FOR DETERMINING AT LEAST ONE VITAL SIGN OF A SUBJECT

CROSS-REFERENCE TO RELATES APPLICATIONS

This application, filed under 35 USC 371, is a United States National Stage Application of International Application No. PCT/IL2019/051295, filed Nov. 27, 2019, which claims priority to IL Application No. 263409, filed on Dec. 2, 2018, the disclosures of which are incorporated herein by reference.

TECHNOLOGICAL FIELD

The present disclosure is in the field of vital signs and physiological parameters detection, specifically by non-invasive measurement of skin motions.

BACKGROUND

Vital signs and various physiological parameters are crucial in monitoring the state of a patient. Many of these physiological parameters are measured by measurement units that are clipped onto, attached or introduced invasively into the patient. When a patient is undergoing long treatment, these measurements can be bothersome, or even may cause harm to the patient. Measuring these vital signs by non-invasive measurement that is taken without the patient being aware of such, may improve conditions for the patient during the period of treatment in a hospital or health center.

GENERAL DESCRIPTION

The present disclosure concerns a system and method for identifying, in a non-invasive manner, internal phenomena/physiological events of a subject, by sampling pressure applied on the external surface of the subject, namely the skin, and determining, based thereon, at least one vital sign. The vital sign can be any physiological parameter, such as heart rate, blood pressure, an organ's activity, intracranial pressure, blood velocity in a predefined path, etc.

In order to determine the vital signs, one or more pressure sensors are placed to sense skin movements of a sensing region of the body skin, whose movements are correlated with a physiological event, such as specific heart activity, e.g. the opening and/or closing of the aortic valve. The pressure sensors are configured to sense movements on a micron-size scale. The pressure sensors can sense the movements indirectly, namely via a layer of a mattress or pillow.

From each sensing region, measurements of the pressure over time, by the sensors sensing the region, are used to generate sensing data. The sensing data is analyzed to generate a pressure variation profile which corresponds to the development of the pressure measurements of a region in time. Predetermined signatures are then recognized in the pressure variation profile, which are expressions of the physiological event, and the time stamps thereof are extracted. The time stamps and/or relations between time stamps are indicative of vital signs of the subject. The present technique uses at least two sensors placed at different locations to be able to obtain a vector force process in place which is not accessible easily, for example inside the cranial region. The sensors are thus placed in proximity to different parts of the body surface. Inner force processes in the body causes pressure changes on the body surface which are then measured by the sensors. In such a way, data obtained by the sensors are synchronous signatures of the true force processes occurring in the body. The predetermined signatures have the same transformation properties as the inner force processes i.e. it is invariant under the same transformation group. The sensors create a coordinate system into which the forces are projected. The force vector can be reconstructed when the force projection is measured in three independent directions. The plurality of sensors enables to obtain a sensing data forming a geometrical object i.e. the signal curve $(\beta_1(t), \beta_2(t), \dots \beta_n(t))$. As soon as the curve changes directions in the n-dimensional space, this can be observed in the corresponding curvature.

In some instances, time stamps from two or more sensing regions are extracted, and a relation between time stamps of different sensing regions is correlative to a vital sign of the subject. For example, time difference between a time stamp correlated with the passage of the blood through the aortic arch, and a time stamp correlated with a pulse wave reflection of the aortic bifurcation, is indicative of a pulse wave propagation velocity.

Therefore, an aspect of the present disclosure provides a system for determining at least one vital sign of a subject. The system includes a plurality of pressure sensors configured to be placed in a vicinity of the subject's body. The sensors can be placed such that they sense movement of the skin indirectly, namely via mediator substances, such as cloths, polymeric players, fabric-based substances etc. In some other embodiments, the sensors can be in direct contact with the skin of the subject to sense directly the movements thereof.

The sensors are configured and operable to sense movements of the skin of the subject's body within one or more regions of the skin of the subject, and generate sensing data corresponding to the at least one region. A region can be associated with a single or a plurality of sensors such that each of the sensors is configured to sense a common physiological event. The physiological event may be for example, bifurcation of the aorta into the common iliac arteries, opening of the aortic valve, the pulse propagation through the aortic arch, contraction of the heart atria, etc. The sensing data comprises a plurality of measured signals being indicative of a common physiological event differentiated in time and intensity from one another. For example, sensors that are configured to sense the propagation of blood along the aortic arch, are disposed at different locations associated with different locations of the aortic arch. As a result of this configuration, the pressure measurements that are expressed on the skin and associated with blood propagation in the aortic arch, differ in time and intensity between different sensors.

Sensing data is generated for each region based on the measurements obtained by the sensors associated with the region, the sensing data comprising a collection of pressure measurements from the sensors associated with the region over time.

The system includes a control unit that is in data communication with each of the plurality of pressure sensors to receive the sensing data, each correlated with a specific region.

The control unit includes an analyzer processing utility configured to analyze the sensing data corresponding to each of the regions, and generate, based thereon, a pressure variation profile for each region. The analyzer processing utility identifies in the pressure variation profile one or more recognizable signatures. These signatures are correlated with an internal physiological event and a signature data is generated based on the identified signatures. The analyzer processing utility, or an extractor module, is configured to extract and generate vital sign data from the signature data indicative of at least one vital sign of the subject. It should be noted that the step of extraction may be performed by the analyzer processing utility, or by another module being in data communication with the analyzer processing utility.

In some embodiments, the extractor module is configured to extract time stamps corresponding to the signature data and generate the vital sign data based thereon.

In some embodiments of the system, the pressure sensors are arranged in a plurality of arrays. The plurality of arrays may include first and second arrays, associated with first and second regions of the skin of the subject. The pressure variation profile is generated for each region based on the sensing data received from the sensors associated with the region. The relations between time stamps may be for example the time difference/delay between linked physiological events in different arrays of sensors. In this connection, it should be understood that the number of arrays used in the technique of the present invention depends on the vital sign to be determined. For example, for measuring the moments of atria contraction, isovolumetric heart muscle contraction and/or aortic valve opening, one array is sufficient. For measuring pulse wave velocity, two arrays are needed.

The first and second regions may be associated with different physiological events and sensing data is generated with respect to each region, namely a first sensing data corresponding to the first region, and a second sensing data corresponding to the second region.

In some embodiments of the system, the control unit is configured and operable to analyze and extract first and second time stamps corresponding to the first and second regions. The time stamps may be related to one another by a consecutive physiological event, namely an event that initiates on a first location that is associated with the first region, and continues to a second location that is associated with the second region. The control unit analyzes and extracts a relation between the first and second time stamps and determines a vital sign based on the relation. The vital sign may include a physiological condition referring to a physiological parameter or physiological state that is derived by the technique of the present disclosure, and is not necessarily measured directly by the pressure sensors. For example, a physiological condition may be derived from an indirect measure, e.g. by calculation based on direct measurements of two physiological events.

In some embodiments, the relation comprises time difference between the first and second time stamp. For example, identifying a time difference between the passage of blood through the aortic arch, and the passage of the blood in the aortic bifurcation, is indicative of the pulse wave propagation.

Pressure sensors associated with the same region may be located in sub-regions arranged in a spaced-apart relationship within the region. Thus, sensors associated with a common region may vary by their pressure measurements of a common physiological event in time and intensity.

In some embodiments, a layer is disposed between the subject's skin and the sensors such that measurement is performed indirectly. The layer may be part of a mattress or a pillow.

In some embodiments of the system, at least some of the sensors are in direct contact with the skin of the subject.

The pressure sensors are configured to sense micron-sized movements of the skin. In some embodiments, the sensors comprise a piezoelectric component. The sensors may further comprise a capacitor component. The piezoelectric component is configured to sense relatively fast signals, and the capacitor component is configured to sense relatively slow signals. In other words, the sensor has a fast sampling rate component configured as a piezoelectric transducer and a slow sampling rate component configured as a capacitor. Examples of such sensors are described in PCT applications with publication Nos. WO 2015/051770, WO 2017/220055 and WO 2017/220056.

In this connection, it should be noted that, in the present disclosure, signals obtained from the plurality of sensors can be related to projections of a certain signal curve to arbitrary axis. This curve can be further described by its Euclidean invariants i.e. the Cartan curvatures (or by the corresponding affine curvatures). Generally, a system of 'n' sensors leads to an n-dimensional curve, which is invariantly described by n−1 curvatures (one dimension is reduced). In some embodiments, for further evaluation of the physiological events, only the first Cartan curvature is used. The inventor has found that higher curvatures contain higher derivatives and are hence more polluted by the noise.

In some embodiments, the control unit is configured and operable to filter out (disregard) signals having a poor signal to noise ratio, such as high curvatures.

In some embodiments, the control unit is configured and operable to process the sensing signals by using a monitoring function being an affine or Euclidian transformation to improve the signal to noise ratio, and to identify personal signatures.

Therefore, in some embodiments of the system, the variation profile, generated based on the sensing data of each region, may be a curvature of an n-dimensional curve, wherein 'n' is the number of pressure sensors that are associated with the corresponding region. In other words, measurements of each sensor of the region, correspond to a one dimensional projection of the n-dimensional signal curve. For example, in the instance of 3 sensors sensing a common region, the signal curve is 3-dimensional. The n-dimensional signal curve may be further described by its geometric invariants called n-dimensional curvatures.

Predetermined signatures of the n-dimensional curvature may be correlated to a rate of change in at least one projection of the signal curve. For example, if the curvature exceeds a predetermined threshold, the analyzer processing utility identifies a signature and the time stamp of the signature is extracted. In some embodiments, the predetermined signature is characterized by a threshold of at least one projection of the signal curve.

In some embodiments of the system, at least one region is associated with one of the head, abdomen, or chest of the subject. In some embodiments a first region is associated with one of the head, abdomen, or chest of the subject, and a second region is associated with an organ other than that associated with the first region.

In some embodiments of the system, the system includes an input module being in data communication with each of the pressure sensors of the plurality of pressure sensors to receive the sensing data corresponding to each of said at least one region. The input module may be also configured to receive biologic-electrical signal data of the subject, the biologic-electrical signal data comprising electrical signatures of physiological events. The extractor module is configured to extract one or more time stamps of the electrical signatures of physiological events from the electrical signal data. Vital sign data is generated based on a relation between time stamps extracted from the electrical signal data, and time stamps extracted from the signatures of the pressure variation profile.

The biologic-electrical signal data may comprise an electrocardiogram (ECG) signal. The ECG signal may provide a time indication of heart activity and the relation between a specific heart activity, and a time stamp derived from a sensing region may be indicative of a vital sign. For example, such an ECG signal may be used in order to identify the initiation of a pulse cycle. It should be noted that if the system is coupled to an ECG device, one array of a plurality of sensors is sufficient to determine at least one vital sign.

In some embodiments, the system further comprises an ECG measurement device configured to provide the biologic-electrical signal data. The sensing signals may be measured simultaneously together with an ECG signal.

In some embodiments, the system measures simultaneously an ECG signal and the signal obtained from all the mechanical sensors with a sampling rate of 1 kHz.

In a specific and non-limiting example, the following steps are performed:
1. The maximum of R wave in the ECG is localized (this is the electric trigger that starts contraction of the heart chambers);
2. The signal from the mechanical sensors starts at the time of the R wave maximum, and ends' second after it is acquired;
3. The curvature is calculated from this signal;
4. The curvature maxima is found from this signal;
5. The next R wave maximum is found, and steps 2-5 are repeated.

The curvature maxima related to the cardiac cycle appear with the same (or similar) time delay with respect to the corresponding R wave. Other maxima, that are not related to the heart cycle and originate for instance from swallowing, fluctuation and similar, are ignored. Each ECG related curvature maximum appears with some time delay after the R wave and this delay remains stable (it changes only slowly).

With sensors placed below the torso, the following can be identified:
1. Aortal valve opening: the related time delay give information about the heart muscle contractility, i.e. how quick the left chamber contracts to create blood pressure that is able to open the aortal valve.
2. The pulse propagation through the aortal arch and diaphragm. This time depends on the aortal stiffness and the thorax pressure.
3. Reflection of the pulse on the abdominal aortal branching into the iliac arteries depending on the aortal stiffness.
4. Aortal valve closing.
5. A maxima can be also related to blood pulse in the kidneys, which are visible only in some patients.

All of this can be measured continuously, whenever the subject does not move. The reactions of the cardiovascular system on administrated medicaments can be observed on-line. Clinically relevant information (for instance the pulse wave velocity along the aorta) can be obtained as well.

With sensors placed below the head, several curvature peaks related to the heart cycle and corresponding to the pulse reflection inside the skull can be identified. The exact reflection time depends on pressure conditions inside the skull and enables to monitor intracranial pressure changes non-invasively.

Another aspect of the present disclosure concerns a method for determining vital signs of a subject. The method includes sensing movements of the skin of one or more regions of the subject, each region being associated with a different physiological event that is expressed on the skin of the subject. The sensing data comprise intensity of pressure measurements over time. For each region, generating sensing data is based on one or more pressure measurements performed in the region. The method further includes analyzing the sensing data and generating a variation profile for the sensing data of each region, and identifying, in each of the pressure variation profiles, one or more signatures indicative of at least one physiological event of the subject. Time stamps are extracted from the identified predetermined signatures, and vital sign data indicative of at least one vital sign of the subject, is generated, based on the extracted time stamps.

In some embodiments of the method, a time relation between different time stamps is determined, the time difference being indicative of the vital sign of the subject. The time relation may be a time difference between time stamps.

Each region may be formed by sub-regions, and the step of sensing movements of the skin comprises sensing for two or more sub-regions.

In some embodiments of the method, the variation profile is a curvature of an n-dimensional curve, wherein 'n' is the number of sub-regions in each region, namely the number of pressure sensors associated with the same region. In other words, all measurements of sensors of the same array are fused to generate an n-dimensional curvature, which can be referred as an "array sensing data" (namely, the Euclidean invariants).

In some embodiments of the method, the pressure variation profile is a curvature of an n-dimensional curvature, wherein 'n' is the number of sub-regions being sensed in the region. The predetermined signature may be characterized by a threshold of a curvature degree, namely a degree of a rate of change in at least one projection of the signal curve.

In some embodiments, the n-dimensional curvature enables to reduce the influence of synchronal vibrations coming from the floor. It should be understood that the force changes caused by a resting human body are small, especially when they are measured by sensors placed below the bed mattress. Vibrations coming from the floor are usually larger. They appear when somebody walks alongside the bed, a door closes, and similar. These vibrations come from the bottom and are transmitted to the sensors from the underside of the bed. This is however a rigid structure that moves as one whole. The signals obtained by different sensors from the underside are therefore similar. If they are identical, the related signal curve will be just a straight line, and its curvature will be equal to zero.

In some embodiments of the method, at least one region is associated with a portion of the head, abdomen, or chest of the subject. In some embodiments at least a first region is associated with one of the head, abdomen or chest of the subject, and a second region is associated with an organ different to that of the first region.

In some embodiments, the method comprises receiving biologic-electrical signal data of the subject. The biologic-electrical signal data comprises electrical signals derived from electrical measurements of the subject. Time stamps of physiological events from the biologic-electrical signal data are extracted and vital sign data is generated based on a relation between time stamps extracted from the biologic-electrical signal data and time stamps extracted from the signatures identified in the pressure variation profile.

The biologic-electrical signal data may comprise data of an ECG signal.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 7B shows a marking of the identified signatures from FIG. 7A as compared with morphology in the invasively measured intracranial pressure pulse waves.

DETAILED DESCRIPTION OF EMBODIMENTS

Figure 1A:
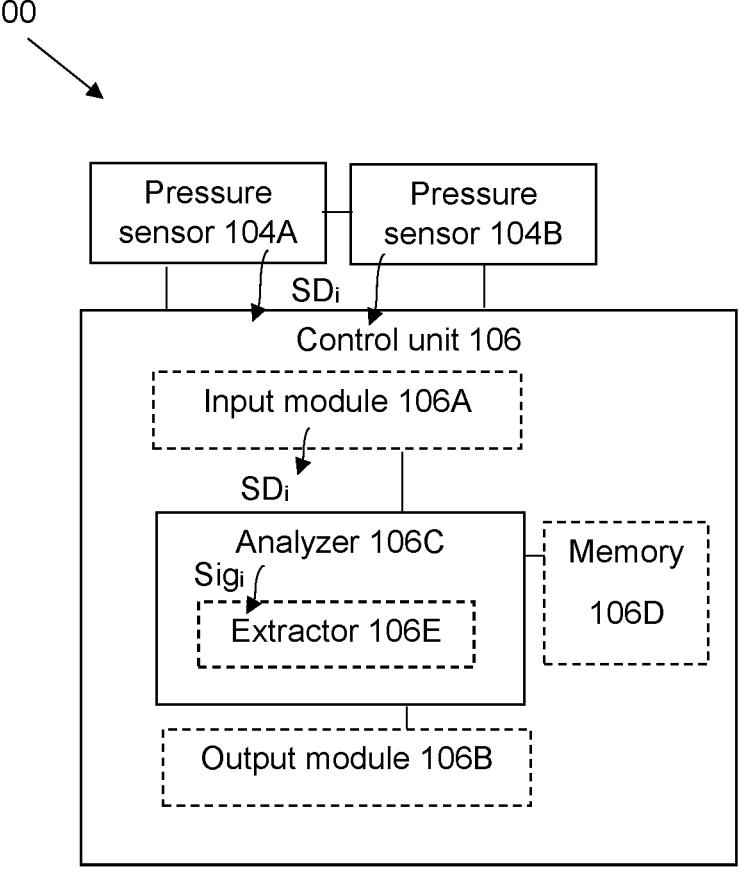
FIGS. 1A-1C are block diagrams of different embodiments of the system according to the present disclosure.

A system according to the present disclosure is exemplified in FIG. 1A, which is a schematic block diagram of the system. The system 100 for determining a vital sign of a subject includes a plurality of pressure sensors 104A, 104 B . . . configured to be placed in a vicinity of the subject's body, and configured and operable to sense movements of skin of the subject's body within at least one region on the skin. Although in the figure, for sake of illustration only, two pressure sensors 104A, 104 B are shown, the invention is not limited to such a configuration, and any desired number of pressure sensors may be used. Measurements from different pressure sensors related to the same sensing region are correlated to a common physiologic event such as propagation of blood through the aortic arch or the opening of the aortic valve. Each pressure sensor is configured to sense pressure from a different sub-region, which constitutes a portion of the sensing region. The pressure sensors 104A, 104B are configured to sense micron-sized movements of the skin. The sensors 104A, 104B may comprise a piezoelectric component. The sensors 104A, 104B may further comprise a capacitor component. The piezoelectric component is configured to sense relatively fast signals, and the capacitor component is configured to sense relatively slow signals. Each sensor has a fast sampling rate component configured as a piezoelectric transducer and a slow sampling rate component configured as a capacitor. Examples of such sensors are described in PCT applications with publication Nos. WO 2015/051770, WO 2017/220055 and WO 2017/220056.

Pressure sensors 104A and 104B generate a sensing data $SD_i$, which is the collection of pressure measurements from all pressure sensors associated with a common sensing region. System 100 comprises a control unit 106 in communication with the pressure sensors 104A and 104B and is configured and operable for receiving and analyzing the sensing data to generate vital sign data indicative of at least one vital sign of the subject. The control unit 106 is configured generally as a computing/electronic utility including inter alia such utilities as data input and output modules/utilities 106A and 106B, memory 106D (i.e. non-volatile computer readable medium), and analyzer/data processing utility 106C. The utilities of the control unit 106 may thus be implemented by suitable circuitry and/or by software and/or hardware components including computer readable code configured for implementing the operations of method 900 shown in FIG. 9 and described below.

The features of the present invention may comprise a general-purpose or special-purpose computer system including various computer hardware components, which are discussed in greater detail below. Features within the scope of the present invention also include computer-readable media for carrying or having computer-executable instructions, computer-readable instructions, or data structures stored thereon. Such computer-readable media may be any available media, which are accessible by a general-purpose or special-purpose computer system. By way of example, without limitation, such computer-readable media can comprise physical storage media such as RAM, ROM, EPROM, flash disk, CD-ROM or other optical disk storage, magnetic disk storage or other magnetic storage devices, or any other media which can be used to carry or store desired program code means in the form of computer-executable instructions, computer-readable instructions, or data structures and which may be accessed by a general-purpose or special-purpose computer system. Computer-readable media may include a computer program or computer application downloadable to the computer system over a network, such as a wide area network (WAN), e.g. Internet.

In this description and in the following claims, a "control unit" is defined as one or more software modules, one or more hardware modules, or combinations thereof, which work together to perform operations on electronic data. For example, the definition of a processing utility includes the hardware components of a personal computer, as well as software modules, such as the operating system of a personal computer. The physical layout of the modules is not relevant. A computer system may include one or more computers coupled via a computer network. Likewise, a computer system may include a single physical device where internal modules (such as a memory and processor) work together to perform operations on electronic data. While any computer system may be mobile, the term "mobile computer system" or the term "mobile computer device" as used herein, especially include laptop computers, netbook computers, cellular telephones, smartphones, wireless telephones, personal digital assistants, portable computers with touch sensitive screens, and the like. Control unit 106 may be comprised of a processor embedded therein running a computer program, or attached thereto. The computer program product may be embodied in one or more computer readable medium(s) having computer readable program code embodied thereon. The computer readable medium may be a computer readable signal medium or a computer readable storage medium. Computer program code for carrying out operations for aspects of the present invention may be written in any combination of one or more programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). These computer program instructions may be provided to the processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. The specified functions of the processor can be implemented by special purpose hardware-based systems that perform the specified functions or acts, or combinations of special purpose hardware and computer instructions.

The control unit 106 or the optional data input module 106A, if any, may include a communication module for receiving the sensing signal data $SD_i$. The sensing data $SD_i$ of each array may thus be communicated to the input module 106A or directly to the control unit 106. The analyzer processing utility 106C receives the sensing data $SD_i$ from the data input module 106A and analyzes it to generate a pressure variation profile for each region being associated with each pressure sensor. The pressure variation profile is generally a profile indicative of difference between pressures which originated from different sensors of a common region. The variation profile is indicative of internal physiological events or phenomena and their expression on the skin surface, constituting together the signal curve, which may be manifested by its Euclidian invariants by a series of functions such as Cartan's curvatures. In some embodiments, by using invariants of group theory (Euclidean, Affine) a time stamp or pattern may be extracted from the signature. The time stamp or pattern may be defined as Cartan and/or affine curvatures which correspond to the pattern of the body force process that is occurring directly inside the body, and for which a direct measurement is not possible. Memory 106D is configured for storing a learning database i.e. preselected data indicative of profiles of the pressure variation profile correlated with an internal physiological event. The database may be implemented with Microsoft Access, Cybase, Oracle, or other suitable commercial database systems. Memory 106D and may be relayed via wireless or wired connection by an external unit to a central database. The processing utility 106C may record the received sensing signal data $SD_i$ in a learning database in memory 106C and/or may query/cross-reference the received sensing signal data $SD_i$ with data in the learning database to identify signatures $Sig_i$ in the pressure variation profile. To this end, the preselected data stored in the learning database may be used to compare the signatures $Sig_i$ in the pressure variation profile with the signatures of an internal physiological event stored in the learning database. The signatures $Sig_i$ are indicative of at least one physiological event of the subject. The processing utility 106C is thus configured to identify in the pressure variation profile for each region, one or more predetermined signatures, and generate signature data thereof. The processing utility 106C or an extractor module 112 is then configured to extract time stamps corresponding to the signature data, and process them to determine at least one vital sign of the subject and generate vital sign data indicative of at least one vital sign of the subject based thereon. Time stamps of the predetermined signatures refer to a certain identifiable time-dependent profile of the signature data. The learning database includes also preselected data indicative of time stamps of the predetermined signatures correlated with at least one vital sign. This last step may be performed by the processing utility 106C or by an extractor module 106E receiving from the processing utility 106C the signatures $Sig_i$ and being capable for extracting time stamps of the signatures and determining at least one vital sign of the subject upon analysis of time stamps of the signatures. The at least one vital sign of the subject may then be outputted by the optional data output module 106B.

Figure 1B:
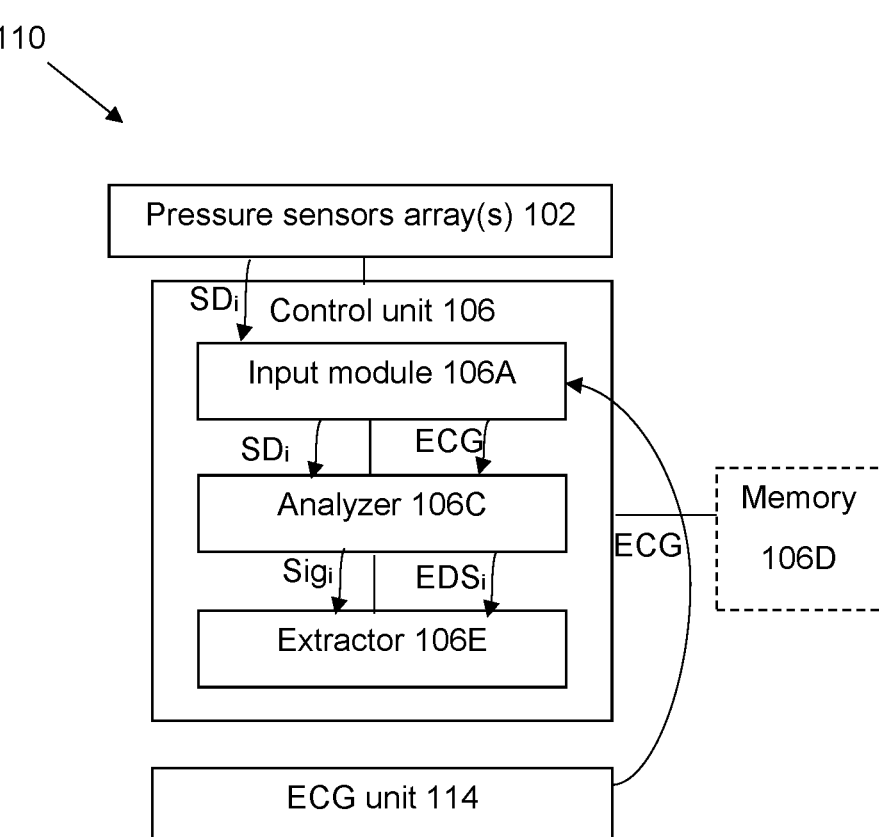
Figure 1C:
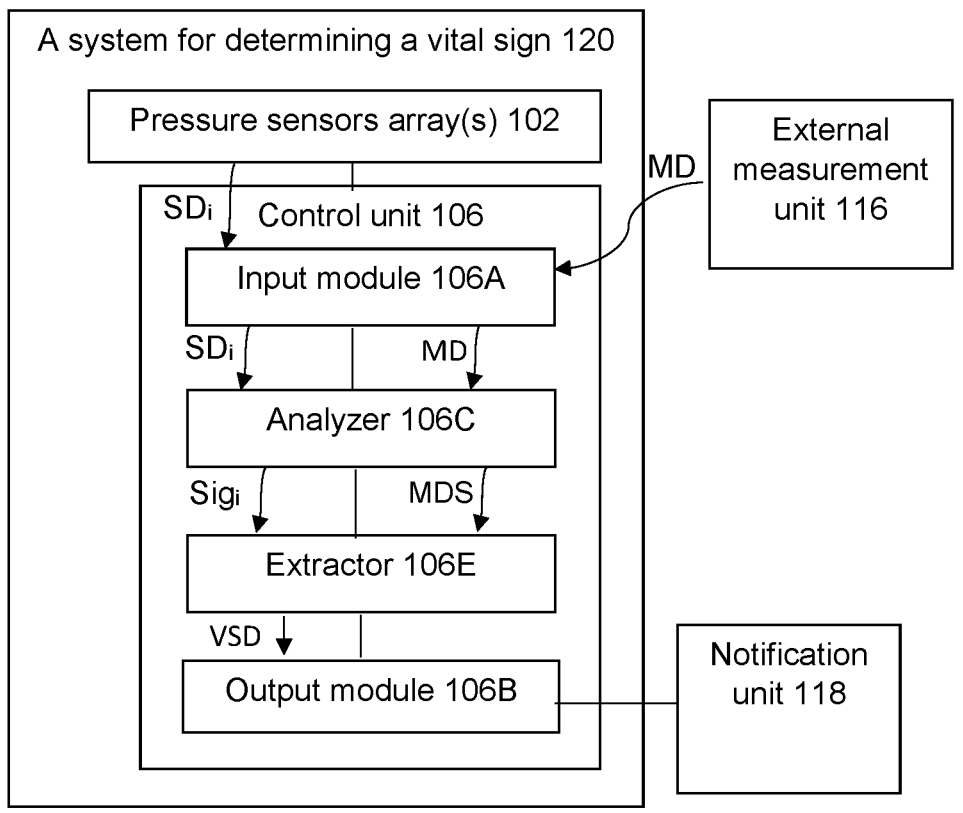

FIGS. 1B-1C are block diagrams of other embodiments of the system according to the present disclosure. The system 110 of FIG. 1B includes one or more pressure sensors arrays 102. For sake of simplicity, one pressure sensors array 102 is shown in the figure. However, the invention is not limited to one pressure sensor array, and any desired number of pressure sensor arrays may be used. Each pressure array 102 includes a plurality of pressure sensors. Each array 102 is associated with a sensing region, which is a location on the surface skin of the subject. The system 110 1B may be connected to an electrocardiogram (ECG) unit 114 that is configured to measure electrocardiogram signals of the subject under inspection, generate electrocardiogram data (ECG) of the subject, and communicate it to the input module 106A. The sensing data $SD_i$ may be measured simultaneously together with the ECG data. The electrocardiogram data ECG is analyzed by the analyzer processing utility 106C and predetermined electrocardiogram signatures EDS are identified.

More specifically, in this case, the learning database of memory 106D comprises preselected data indicative of electrocardiogram signatures $EDS_i$ correlated with internal physiological parameters and/or specific physiological events. The preselected data is used to compare the signatures EDS with the preselected signatures stored in the learning database and to correlate between identified signatures and specific physiological events according to their relation to the electric-cardiogram signatures $EDS_i$. Alternatively and additionally, extractor module 106E may extract electrocardiogram time stamps therefrom to find a relation between them and the time stamps extracted from the identified signatures $Sig_i$. By finding the relation between the time stamps of the two measurements (i.e. pressure-based and electrical based measurement), internal physiological parameter or at least one vital sign of the subject can be determined. FIG. 1C shows another embodiment of the system 120 of the present disclosure. The system 130 differs from that of FIG. 1A in that it receives measured data MD from an external measurement unit 116 such as an ECG unit, pulse measurement device etc. The external measurement unit 116 generates the measurement data MD and transmits it to the input module 106A. The external measured data MD is analyzed by the analyzer processing utility 106C and measurement data signatures MDS are identified. Time stamps thereof are then extracted from measurement data signatures MDS by the extractor module 106E so as to generate, based thereon, vital sign data VSD. The vital sign data VSD comprises data related to at least one vital sign or physiological parameter of the subject and it may be transmitted to an external notification unit 118, such as a monitor or an audio speaker, via the data output module 106B to output the vital sign data to a user.

Figure 2:
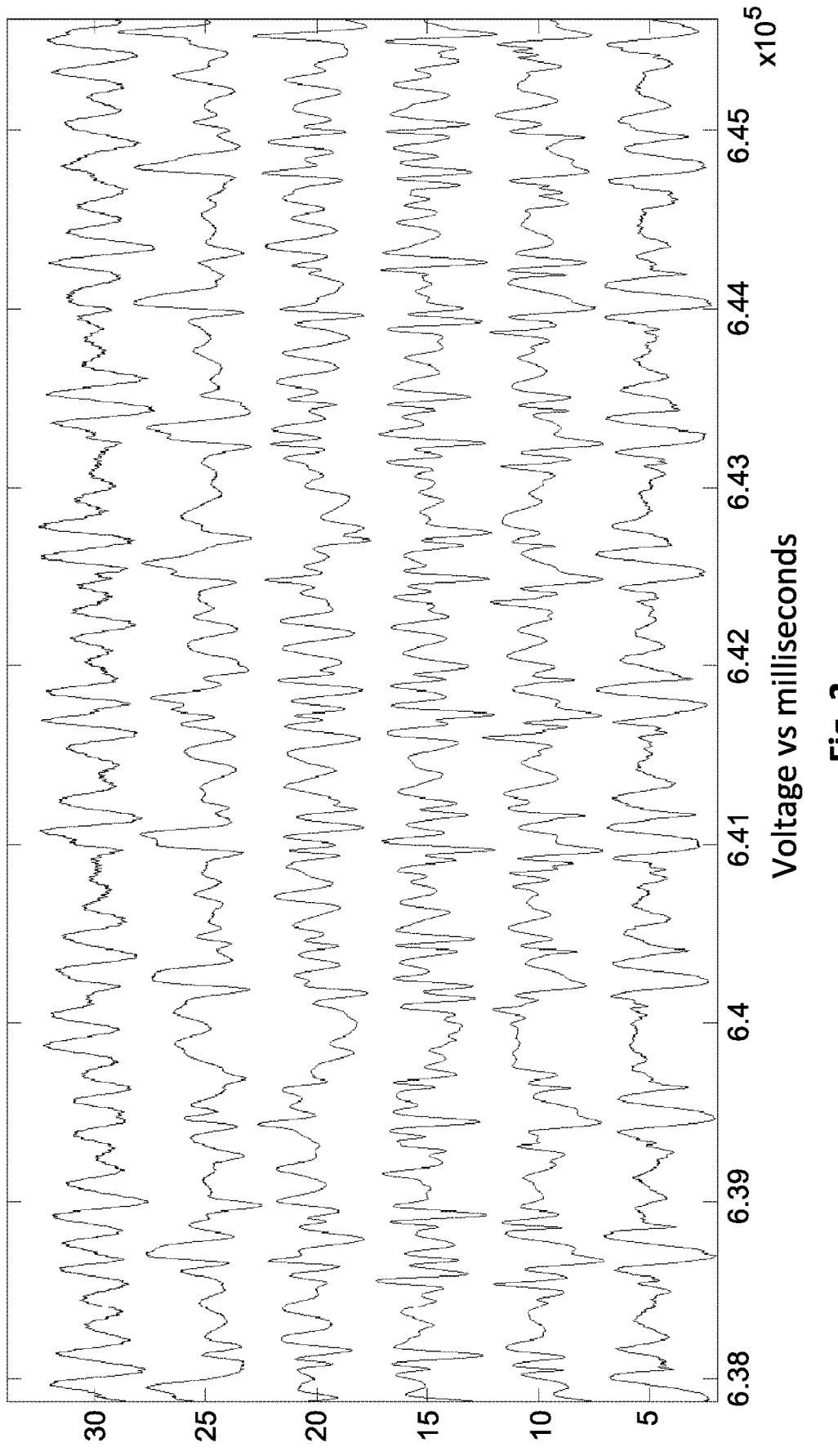
FIG. 2 is an example of data presentation received from the measurement of six pressure sensors.

As described above, each sensing region is sensed by an array of a plurality of sensors being configured to generate sensing data that can undergo further analysis to derive the vital sign of the subject. Each sensor of the array is configured to sense from a different sub-region that is comprised within the sensing region. FIG. 2 shows a graph illustrating an example of an array of six sensors sensing from six sub-regions of a common sensing region. The graph presents the normalized voltage of the pressure sensed by each sensor over time, wherein the voltage of the $n^{th}$ sensor has been shifted by 5 multiplied by n for visualization convenience. This is an example of sensing data $SD_i$ that is generated by the sensors and communicated to the control unit for further analysis.

In the figures throughout the application, like elements of different figures were given similar reference numerals shifted by the number of hundreds corresponding to the number of the figures. For example, element 304 in FIG. 3 serves the same function as element 104 in FIGS. 1A-1C.

Figure 3:
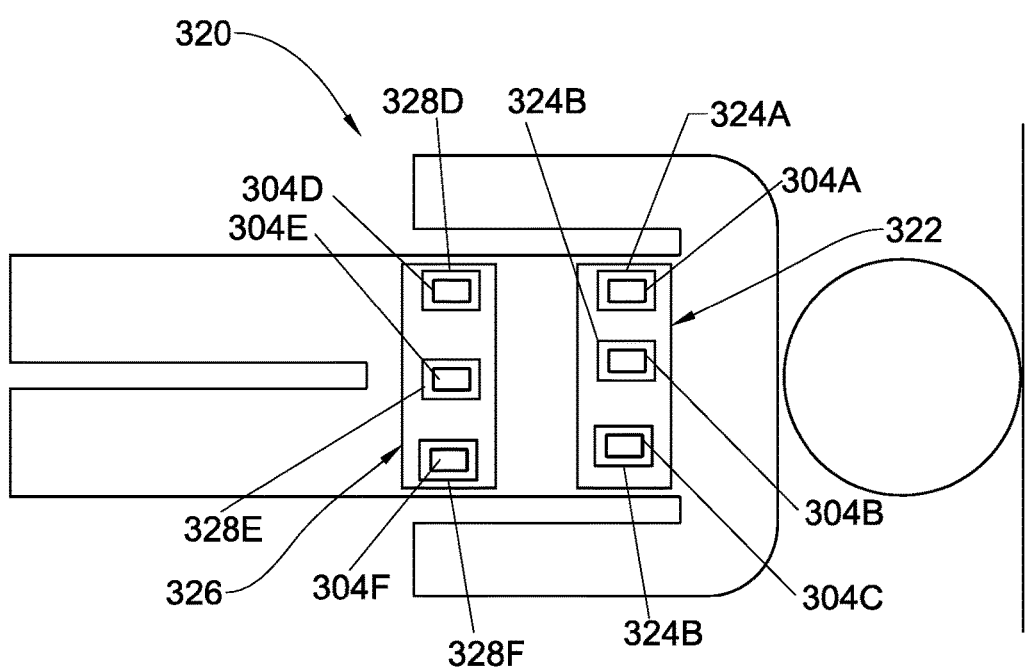
FIG. 3 is a schematic illustration of an example of a sensor array for sensing different regions of a patient that lies horizontally.

FIG. 3 is a schematic illustration of a top view of a subject with indications of regions and sub-regions being sensed on the subject's skin. In this specific and non-limiting example, the subject 320 lies on a patient's bed that accommodates two arrays of sensors, each of the arrays having three pressure sensors. The plurality of pressure sensors is arranged in an optimized arrangement, in order to monitor various biological/physiological parameters. In some embodiments, this technique may utilize a preliminary stage of selection of the sensing signals of certain measurement sessions performed by a desired group/array of the plurality of pressure sensors and also selection of the predetermined time intervals. The processing of the measured signals from the multiple sensors may also utilize comparison between the signals measured by different sensors arranged with a known distance between them.

Figure 4:
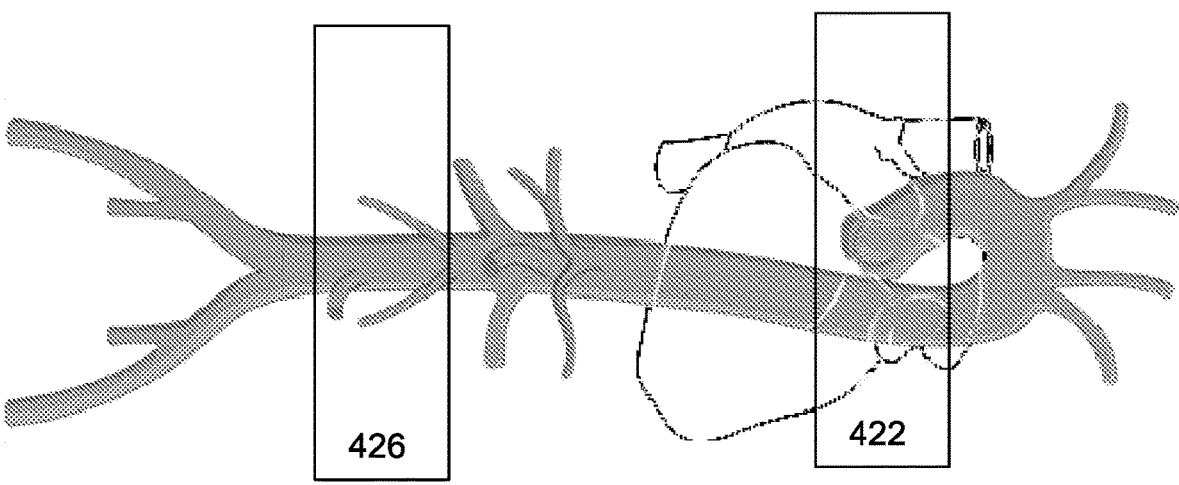
FIG. 4 is a schematic illustration of the aorta that demonstrates different portions that are measured by the noninvasive system and method of the present disclosure.

The pressure sensors can sense movements of a micron-size scale directly (e.g. upon physical contact with the skin of subject) or indirectly, namely via a layer (not shown) of a mattress or pillow. A layer (not shown) can thus be disposed between the subject's skin and the sensors. The layer may be a portion of a mattress or a pillow. In the example, the first array is configured to sense a portion of the chest region 322 of the subject. Each of the sensors 304A, 304B, 304C is configured to sense a corresponding sub-region 324A, 324B, 324C. The second array is configured to sense a portion of the abdomen region 326. Each of the sensors 304D, 304E, 304F is configured to sense a corresponding sub-region 328D, 328E, 328F. Therefore, sensors 304A, 304B, 304C generate a first sensing data and sensors 304D, 304E, 304F generate a second sensing data. The first sensing data, derived from the chest region 322, comprises data indicative of physiological events which occur in the chest and its vicinity. For example, the first sensing data may comprise data relating to the opening of the aortic valve and blood passage through the aortic arch. Each of the sensors 304A, 304B, 304C measures pressure on the skin surface of the subject 320, differentiated in time and intensities from the other sensors. However, it should be understood that the sensing data from each sensor is correlated to the same internal physiological events. This is exemplified in FIG. 4, which is an illustration of the aorta, including the aortic arch. These measurements constitute data for generating the pressure variation profile in regions 422 and 426. Sensors 304A, 304B, 304C of FIG. 3 generate sensing data indicative of physiological events occurring in the chest, and sensors 304D, 304E, 304F generate sensing data indicative of physiological events in the abdomen and its vicinity. For example, a physiological event in the abdomen may be bifurcation of the aorta into the common iliac arteries. In the same manner, sensors 304D, 304E, 304F measure pressure on the skin surface of the subject 320, differentiated in time and intensities from the other sensors, but correlated to the same internal physiological events.

Figure 5:
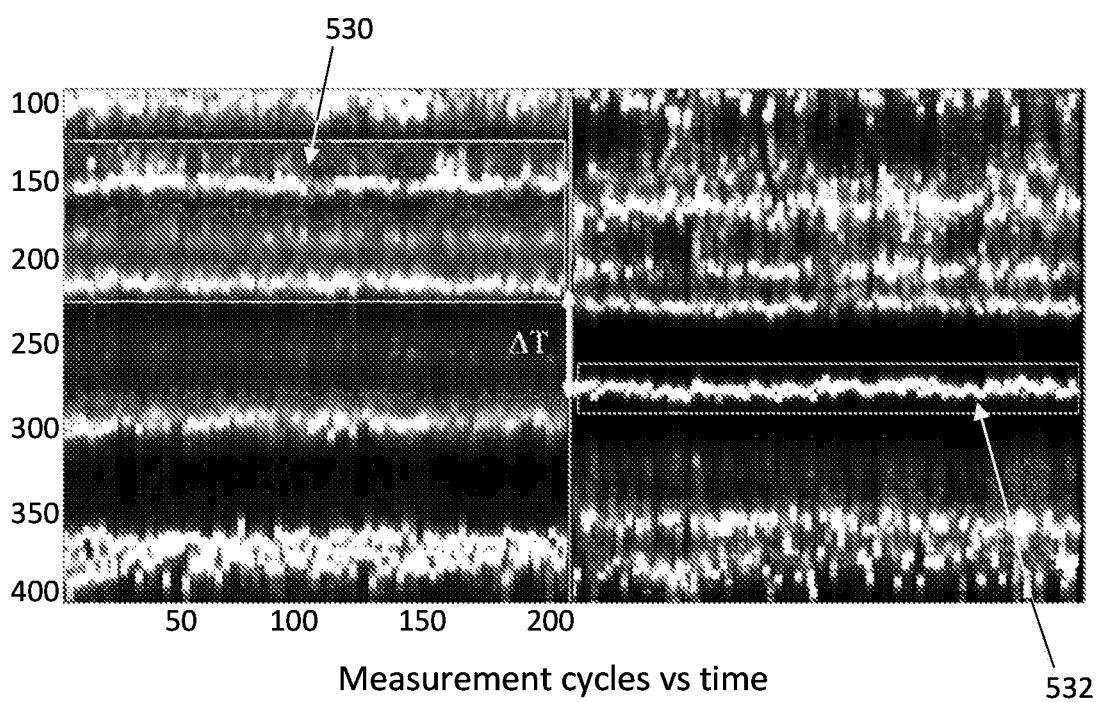
FIG. 5 is a chart of an example of presentation of the pressure variation profile having a curvature variation profile that is generated based on measurement of the pressure sensors.

An example of a presentation of the pressure variation profile is shown in a chart in FIG. 5. FIG. 5 shows the pressure variation profile as generated by the control unit as a function of time in milliseconds. The obtained data are synchronized with respect to the R-wave of the corresponding ECG signal that is localized at 100 ms. The bright areas represent a value of the first Cartan curvature of the pressure variation profile. The brighter the area, the greater the curvature. The dark areas represent times with low pressure variation curvature. As can be seen, there are gray and white areas that have a constant time delay with respect to the R-wave of the corresponding ECG signal (R wave is localized at 100 ms). They represent curvature changes related to heart muscle contraction and blood ejection (note that the R-wave serves as a trigger for heart contraction). There are also areas characterized by alternating and noisy brightness, which represent a pressure variation profile that is not related to the triggering R-wave and is dominated by background noise or subject motion. In this specific and non-limiting example, the left side of the chart is the pressure variation profile generated based on a first sensing data, derived from a sensing region associated with the chest of a subject, and the right side of the chart is the pressure variation profile generated based on a second sensing data, derived from a sensing region associated with the abdomen of a subject. The areas of interest are identified, 530 on the left side of the chart, and 532 on the right side, and the time of these areas of interest is determined. The time of each of the areas of interest can be determined based on an average of a plurality of measurement cycles or based on a single measurement cycle. These areas of interest are representations of internal physiological events and are indicative of a physiological condition or parameter of the subject. In this example, area 530 represents two physiological events, the opening of the aorta, which is represented by the top bright line in area 530, and the pulse propagation through the aortic arch, which is represented by the bottom bright line in area 530. Area 532 represents a reflection of bifurcation of the blood in the abdomen.

The time difference between the times of the physiological events, namely the time difference DT between the time stamps thereof, are indicative of a vital sign of the subject. In this example, the time difference between the propagation of the pulse through the aortic arch and the bifurcation of the blood in the abdomen is indicative of the pulse wave propagation velocity. By knowing the distance the blood travels between the aortic arch and the bifurcation in the abdomen, the wave propagation velocity can be calculated. The distance may be obtained according to some parameters of the subject, such as age, gender, etc., which are known from the literature.

This kind of measurement can be taken continuously while a patient lies on a patient's bed without the need to physically connect the patient to any measurement device. The sensors can be embedded within the patient's bed, e.g. in the mattress or below the mattress, and sense the micro-movements of the patient, as long as the patient lies on the bed and generally does not move.

13

14

Figure 6:
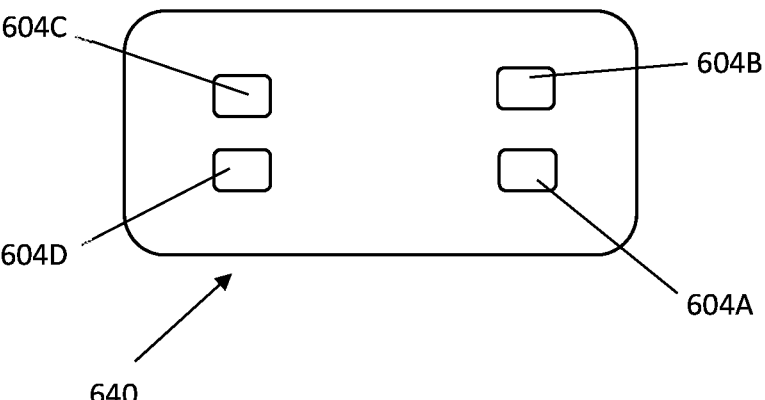
FIG. 6 is a schematic illustration of a sensor array in a head-pressure measuring unit.

FIG. 6 is a schematic illustration of an array of sensors which can be accommodated in a head measuring unit such as a pillow. As can be appreciated, sensors 604A and 604B are arranged at one side of the pillow 640, and sensors 604C and 604D are arranged on the other side. This configuration allows to measure sufficient data from micro-movements of the skin surface of the head to determine data indicative of the intracranial pressure of the subject.

The measurement of vital signs from micro-movements of the head is similar to the speed pulse rate detection. From the measured motion of the head, the Cartan invariants are counted, namely the pressure variation profile is generated, and the corresponding events and signatures, are found. To determine the value of intracranial pressure, the time lag/difference between these events and an ECG R-wave of QRS complex of the ECG is extracted and calculated.

Without being bounded to theory, the following is an example of finding the relation between the time lag/difference between the events detected in the head and the ECG R-wave.

If the Moens-Korteweg equation is translated into arterial pressure, the relation $V \sim a\sqrt{P}$, is obtained, where a is a constant, V is the pulse velocity and P is the arterial pressure.

By determining the pulse wave propagation velocity, the corresponding arterial pressure can be calculated. This is commonly used in pressure estimation by pulse wave pulse measurement. However, this relationship is also related to noninvasive measurement of intracranial pressure. In the cranial cavity, the arteries are embedded in a non-zero pressure environment. From the point of view of the artery, this means that pressure on its wall comprises arterial pressure, from which the intracranial pressure is related, according to the following equation:

$$CPP=MAP-ICP$$

where CPP is arterial wall pressure (perfusion pressure), MAP is mean arterial pressure and ICP is mean intracranial pressure. According to the above, this may lead to the assumption:

$$\Delta T \sim \frac{1}{V} \sim \frac{1}{\sqrt{MAP-ICP}} \sim a(ICP-MAP),$$

where a is a constant. In order to determine the MAP, the arterial pressure may be measured, preferably on the patient's hands.

Delay time $\Delta T$ is the time difference between the ECG R-wave and the moment of the event detected in inversions from the head being measured. If intracranial pressure increases, the time difference increases, and vice versa. In fact, there are several events in the head that essentially duplicate the morphology of the invasively measured intracranial pulse.

Intracranial pulse-induced cardiac activity usually contains 3 maximas known as P1, P2 and P3 (ICP pulse morphology).

Figure 7A:
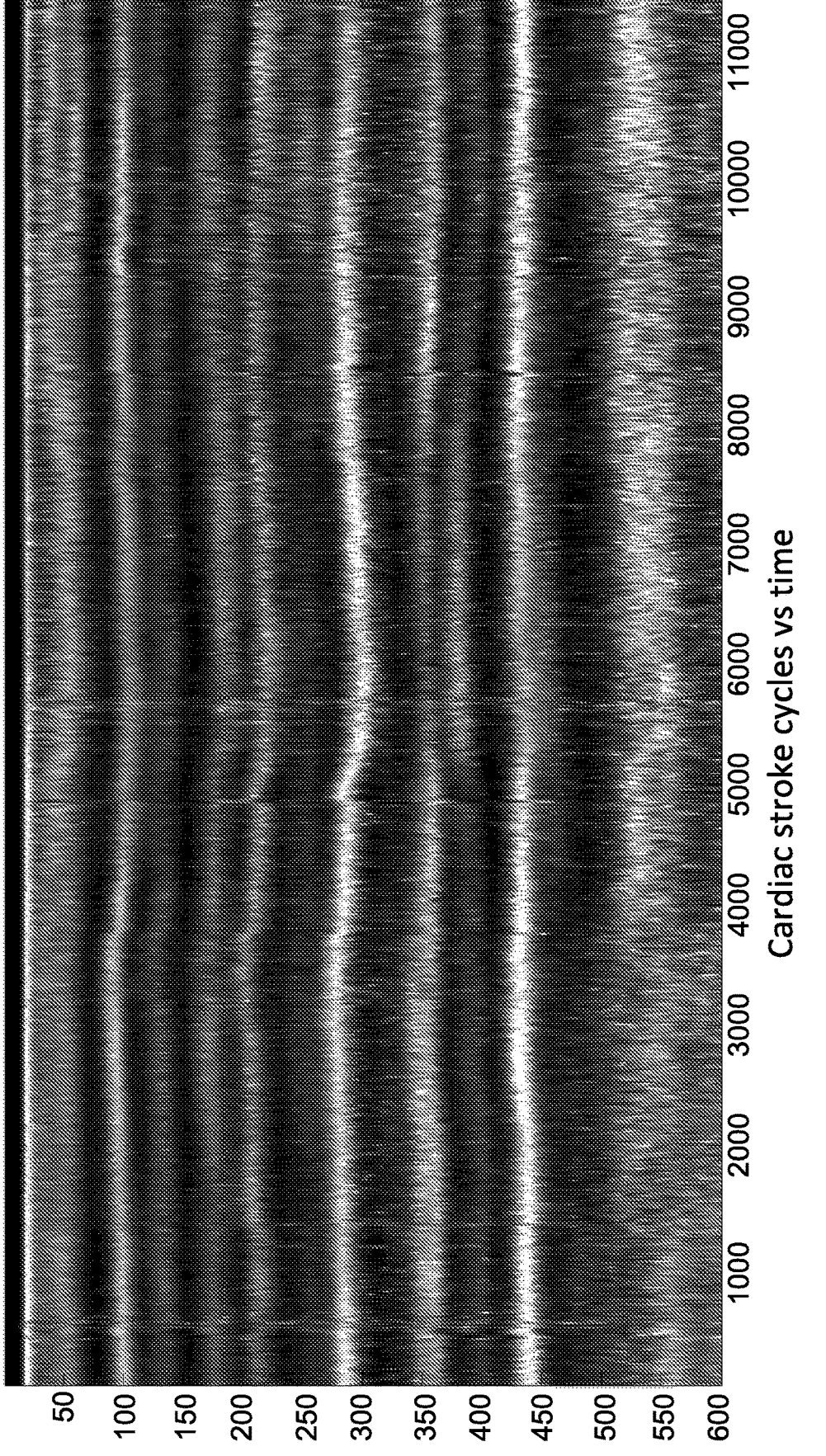
FIGS. 7A-7B are examples of presentations of the pressure variation profile having a curvature variation profile that is generated based on sensing data of 4 sensors that sensed micro motions from the head of a subject.
Figure 7B:
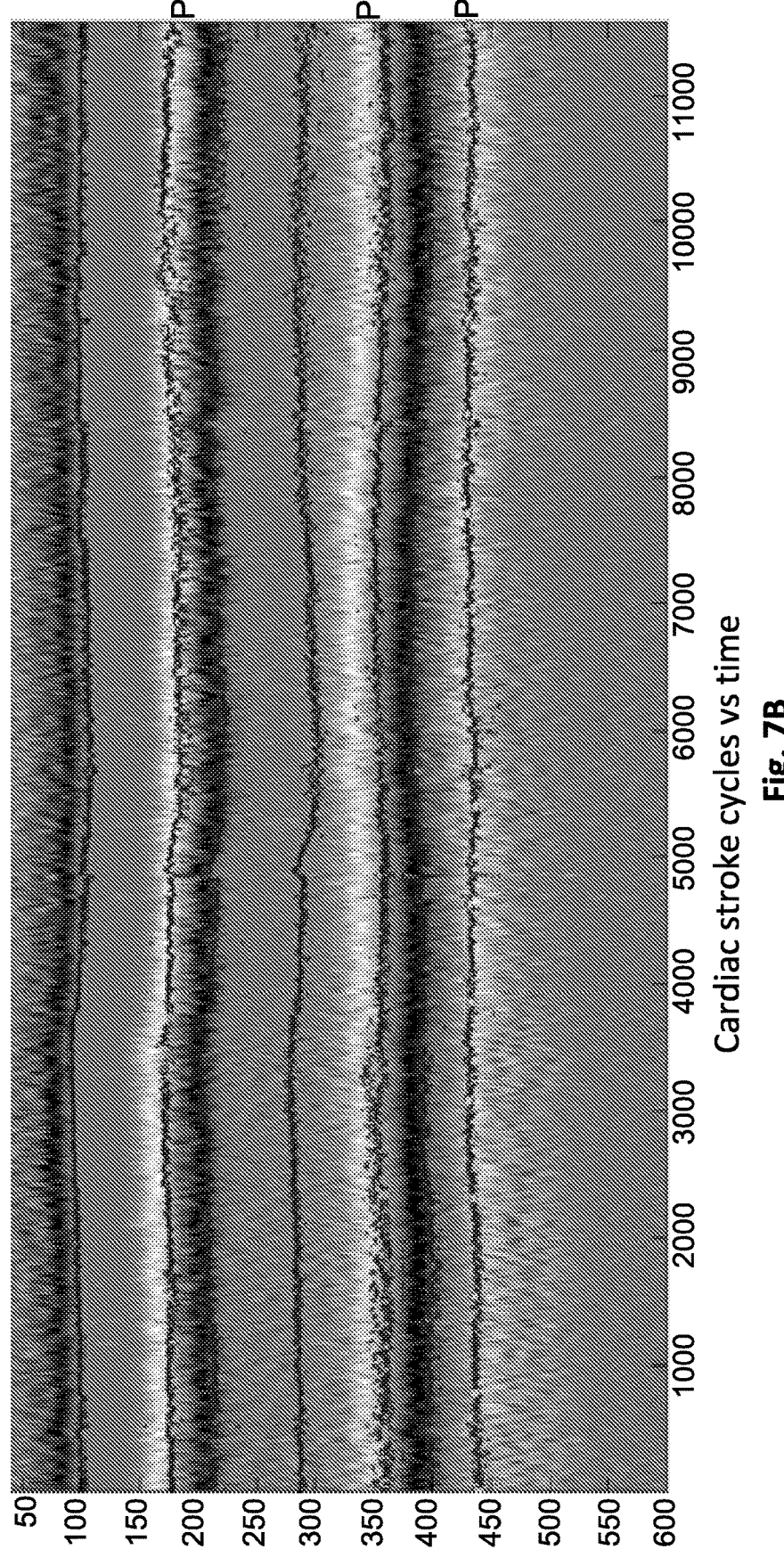

The inventors found that the data of the invasively measured ICP wave morphology corresponds to mechanical phenomena in the head, which subsequently manifests itself as events in the corresponding invariant. This is demonstrated in FIGS. 7A-7B illustrating cardiac stroke cycles vs. time in milliseconds. FIG. 7A is a mechanical invariant, counted with 4 headrest sensors (as illustrated in FIG. 6 above) for time intervals that start with R-wave ECG and end with 600 milliseconds (time-lock). In this connection, it should be noted that the evaluation of ICP can be done with an array of two sensors placed under the patient's head. An array of four mechanical sensors can also be used as shown in FIG. 6, configured to provide complex head motions from more directions, and therefore better resolution. The individual invariants, namely the measurement cycles, are arranged next to each other so that consecutive heart strokes are presented along the X-axis, while the corresponding calculated invariant is displayed on the Y-axis. The result is a two-dimensional map on which signatures of events (maximum invariants) are displayed. In other words, a bright colored area represents a relatively high rate of curvature change, and a dark colored area represents a relatively low rate of curvature change. There are total of 11568 consecutive cardiac strokes shown in FIGS. 7A-7B.

The extracted time stamps of the identified signatures of events are shown in FIG. 7B together with the invasively measured intracranial pressure. The identified signatures are marked in the figure as the lines corresponding to P1, P2 and P3. As can be appreciated, the events represent the morphology of the invasively measured pulse wave, including their changes over time (corresponding to the maxima of P1, P2, P3).

Figure 8:
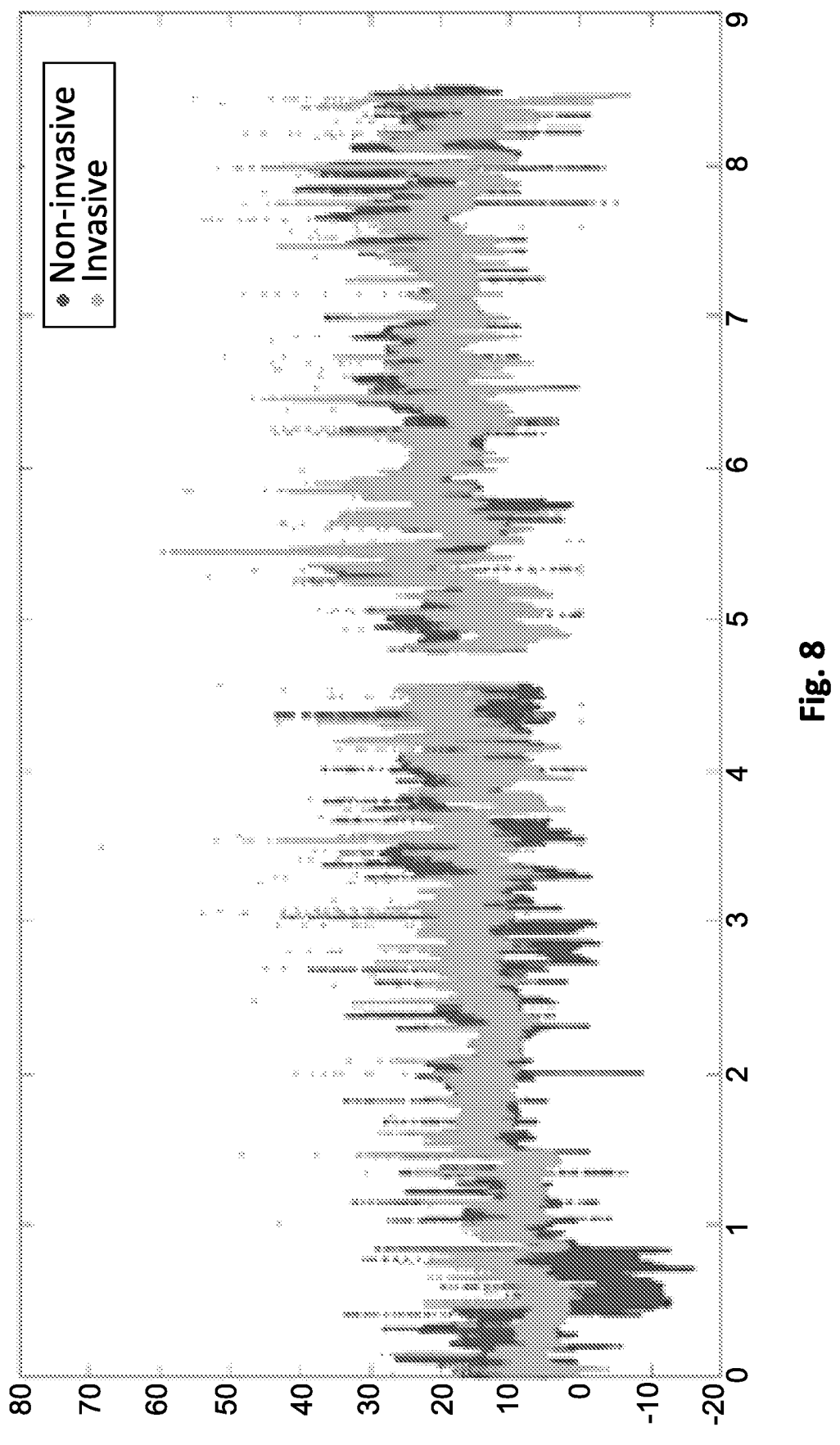
FIG. 8 is a chart of comparative data between noninvasive measurement of the present disclosure, and conventional invasive measurement of intracranial pressure.

FIG. 8 shows comparative data between the present disclosure's non-invasive measurement, and an invasive measurement of ICP of a patient. The figure presents data of consecutive 8-day measurement, in which the dark grey areas represent the present disclosure's non-invasive measurements, and the light grey areas the invasive measurements. The non-invasive method correctly follows long-term trends in intracranial pressure changes. Local mismatches are mostly driven by patient movements on the bed, which also lead to inaccuracies in invasive measurement.

Figure 9:
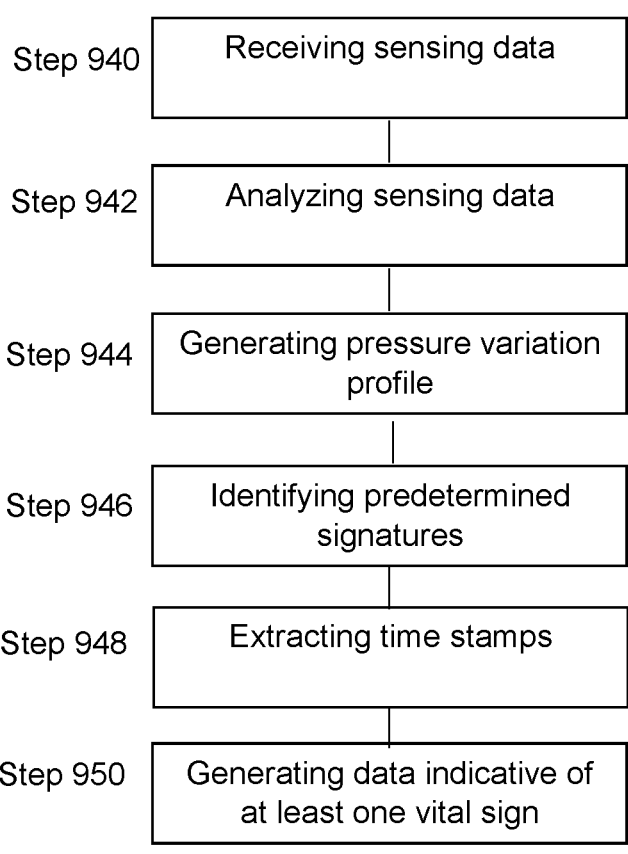
FIG. 9 is a flow diagram of a method for determining a vital sign of a subject according to the present disclosure.

FIG. 9 is a flow diagram of an example of a method for carrying out the invention of the present disclosure for determining a vital sign of a subject. The method includes receiving sensing data step 940 of pressure measurements from one or more regions of the skin surface of a subject. The sensing data is analyzed step 942 to generate a pressure variation profile step 944 of the measurements. Predetermined signatures are identified step 946 in the pressure variation profile, and the predetermined signatures are indicative of internal physiological events that are expressed on the skin surface of the subject. Time stamps of the identified predetermined signatures are extracted step 948 and, based on the extracted time stamps, data indicative of at least one vital sign is generated step 950. The data may be generated based on a single time stamp or any relation between two or more time stamps of the identified predetermined signatures.

The invention claimed is:

1. A system for determining at least one vital sign of a subject, the system comprising:

a plurality of pressure sensors configured to be placed in a vicinity of the subject's body, and configured and operable to sense movements of skin of the subject's body within at least one region on the skin and generate sensing data corresponding to said at least one region; said at least one region comprising two or more separate locations on the skin, the sensing data comprises a plurality of measured signals being indicative of a common physiological event differentiated in time and intensity from one another;

a control unit in data communication with each pressure sensor of the plurality of pressure sensors wherein each pressure sensor of the plurality of pressure sensors comprises a piezoelectric component and a capacitor component, said control unit comprising an analyzer processing utility configured and operable to:

receive the sensing data corresponding to each of said at least one region;

generate, for the pressure sensors associated with each of said at least one region, a pressure variation profile for said region, wherein the pressure variation profile is a curvature of an n-dimensional curve, wherein "n" is the number of pressure sensors associated with the same region;

identify one or more predetermined electrical signal signatures within the pressure variation profile indicative of at least one physiological event of the subject;

generate signature data of the at least one physiological event of the subject; and extract at least one time stamp from said signature data; and generate vital sign data indicative of at least one vital sign of the subject based on the at least one time stamp.

2. The system of claim 1, wherein said plurality of the pressure sensors are arranged in at least first and second arrays located in vicinities of first and second different regions of the subject's body, respectively, and providing corresponding first and second sensing data indicative of movements of the skin in the first and second regions and wherein the first and second sensing data are indicative of different physiological events.

3. The system of claim 1, wherein said control unit is configured and operable to analyze first and second electrical signal signatures of the predetermined electrical signal signatures and corresponding first and second time stamps, and determine a relation between the first and second time stamps, said relation being indicative of at least one physiological condition of the subject's body, and wherein the relation comprises time difference.

4. The system of claim 1, wherein the pressure sensors associated with a same region are located in sub-regions arranged in a spaced-apart relationship within said same region.

5. The system of claim 1, wherein a layer is disposed between the subject's skin and each of the plurality of pressure sensors, wherein the layer is a part of a mattress or a pillow.

6. The system of claim 1, wherein the sensing data comprises intensity of pressure samples of each one of the plurality of pressure sensors over time.

7. The system of claim 1, wherein at least one region is a part of the head of the subject.

8. The system of claim 1, wherein at least one region is a part of the abdomen and at least a second region is a part of the chest of the subject.

9. The system of claim 1, further comprising an input module being in data communication with each of pressure sensors of the plurality of pressure sensors to receive the sensing data corresponding to each of said at least one region.

10. The system of claim 9, wherein the input module is configured to receive electrical signal data of the subject; and the analyzer processing utility is configured to extract one or more time stamps of physiological events from the electrical signal data and generate vital sign data indicative of at least one vital sign of the subject based on a relation between the one or more time stamps extracted from the electrical signal data and the at least one time stamp extracted from the one or more predetermined electrical signal signatures identified in the pressure variation profile.

11. The system of claim 10, wherein the electrical signal data comprises an ECG signal.

12. The system of claim 1, wherein the at least one vital sign is at least one of pulse wave propagation velocity and intracranial pressure.

13. A system for determining at least one vital sign of a subject, the system comprising:

a plurality of pressure sensors configured to be placed in a vicinity of the subject's body, and configured and operable to sense movements of skin of the subject's body within at least one region on the skin and generate sensing data corresponding to said at least one region; said sensing data comprising a plurality of measured signals being indicative of a common physiological event differentiated in time and intensity from one another;

a control unit in data communication with each pressure sensor of the plurality of pressure sensors; said control unit comprising an analyzer processing utility configured and operable to:

receive the sensing data corresponding to each of said at least one region;

generate, for the pressure sensors associated with each of said at least one region, a pressure variation profile for said region, wherein the pressure variation profile is a curvature of an n-dimensional curve, wherein "n" is the number of pressure sensors associated with the same region;

identify one or more predetermined electrical signal signatures within the pressure variation profile indicative of at least one physiological event of the subject;

generate signature data of the at least one physiological event of the subject; and extract at least one time stamp from said signature data; and generate vital sign data indicative of at least one vital sign of the subject based on the at least one time stamp, wherein the n-dimensional curve is a geometrical object formed by the sensing data sensed by the plurality of pressure sensors and wherein the predetermined electrical signal signatures are characterized by a threshold of at least one projection of the n-dimensional curve.

14. A system for determining at least one vital sign of a subject's head, the system comprising:

a plurality of pressure sensors configured to be placed in a vicinity of the subject's head, and configured and operable to sense micro motions of the subject's head within at least one region on the head and generate sensing data corresponding to said at least one region; said at least one region comprising two or more separate locations on the skin, wherein the sensing data comprises a plurality of measured signals being indicative of a common physiological event differentiated in time and intensity from one another;

a control unit in data communication with each pressure sensor of the plurality of pressure sensors wherein each pressure sensor of the plurality of pressure sensors comprises a piezoelectric pressure sensor configured to sense signals at a first sampling rate and a capacitive pressure sensor configured to sense signals at a second sampling rate slower than the first sampling rate, said control unit comprising an analyzer processing utility configured and operable to:

receive the sensing data corresponding to each of said at least one region;

generate, for the pressure sensors associated with each of said at least one region, a pressure variation profile for said region, wherein the pressure variation profile is a curvature of an n-dimensional curve, wherein "n" is the number of pressure sensors associated with the same region;

identify one or more predetermined electrical signal signatures within the pressure variation profile indicative of at least one physiological event of the subject;

generate signature data of the at least one physiological event of the subject; and extract at least one time stamp from said signature data; and generate vital sign data indicative of at least one vital sign of the subject based on the at least one time stamp.

\* \* \* \* \*